US005720975A

United States Patent [19]
Etzel

[11] Patent Number: 5,720,975
[45] Date of Patent: Feb. 24, 1998

[54] USE OF INCENSE IN THE TREATMENT OF ALZHEIMER'S DISEASE

[76] Inventor: Rainer Etzel, Karl-Theodor-Strasse 14, D-82343 Pocking/Possenhofen, Germany

[21] Appl. No.: 796,857

[22] Filed: Feb. 5, 1997

Related U.S. Application Data

[63] Continuation of Ser. No. 370,886, Jan. 10, 1995, abandoned.

[30] Foreign Application Priority Data

Dec. 13, 1994 [DE] Germany ............ 44 44 288.2

[51] Int. Cl.$^6$ ................................. A61K 9/20
[52] U.S. Cl. .................. 424/464; 514/784; 514/766
[58] Field of Search ................ 424/464; 514/784, 514/766

[56] References Cited

U.S. PATENT DOCUMENTS 5,064,823 11/1991 Lee et al. ................. 514/198
5,280,119 1/1994 Spielvogel et al. ......... 544/229
5,494,668 2/1996 Patwardham .............. 424/195.1

*Primary Examiner*—James J. Seidleck
*Assistant Examiner*—Michael A. Williamson
*Attorney, Agent, or Firm*—Burns, Doane, Swecker & Mathis, L.L.P.

[57] ABSTRACT

The invention relates to the use of incense (olibanum), incense extracts, substances contained in incense, their physiologically acceptable salts, their derivatives and their physiological salts, pure boswellic acid, of a physiologically acceptable salts, of a derivative, of a salt of the derivative, for production of a medicament for the prevention or treatment of Alzheimer's disease.

8 Claims, No Drawings

USE OF INCENSE IN THE TREATMENT OF ALZHEIMER'S DISEASE

This application is a continuation of application Ser. No. 08/370,886, filed Jan. 10, 1995, now abandoned.

DESCRIPTION

The invention relates to the use of incense (olibanum), incense extracts, substances contained in incense, their physiologically acceptable salts, their derivatives and their physiological salts, pure boswellic acid, of a physiologically acceptable salt, of a derivative, of a salt of the derivative, for production of a medicament for the prophylactic and therapeutic treatment of Alzheimer's disease (Morbus Alzheimer).

The invention also relates to the use of incense (olibanum), incense extracts, substances containing incense, their physiologically acceptable salts, their derivatives and their physiological salts, pure boswellic acid, of a physiologically acceptable salt, of a derivative, of a salt of the derivative, for the prevention or treatment of Alzheimer's disease.

Alzheimer's disease is a degenerative disease that generally appears from the fifties on with morphological and biochemical changes in the brain regions, especially in the area of the hippocampus and the association cortex. Currently a distinct increase in the morbidity rate is being observed. The symptoms of this disease are disorientation with disruption of cognitive capabilities, loss of memory and changes in character with emotional instability, total regression to the point of needing complete care, and dementia.

Approximately 850,000 people suffer from Alzheimer's disease in Germany; worldwide approximately 15 million people are affected.

The therapeutic possibilities for the treatment of this disease have been unsatisfactory to this point. Since the cause for the development of Alzheimer's disease is still unknown, no directly effective therapies are available. Also, there are no medicaments that at least relieve the symptoms of Alzheimer's disease.

The therapeutic attempts known until now are not satisfactory and have no clinical relevance. For one, the currently approved medicament, Tacrine, with a low response rate, unsatisfactory therapeutic results and above all clearly hepatotoxic side effects, is only mildly satisfactory for long-term therapy. Attempts with monosialogangliosides as a growth factor stimulant of the nerve cells remain without significant effect.

The invention lays the basis for making the use of medications that serve the treatment of Alzheimer's disease available. The compound made available in accordance with this invention should, in addition, be in a position to prevent or delay the development of Alzheimer's disease. The drug, in accordance with this invention, should be nontoxic and easily tolerated by the patients.

It was surprisingly just discovered that incense (olibanum), incense extracts, substances contained in incense, their physiologically acceptable salts, their derivatives and their physiological salts, pure boswellic acid, a physiologically acceptable salt, a derivative, a salt of the derivative are exceptionally effective for the treatment of Alzheimer's disease.

Drugs, which contain compounds from the boswellia serrata plant are used to treat inflammation, but also rheumatism in the ayurvedic system of medicine in India. The advice to use this drug in the treatment of Alzheimer's disease cannot be found in any literature. Based on the biological activities of the material contained in the boswellia serrata, one tries to explain its structure. Pardhy & Bhattacharyya report in the Ind. J. Chem., 16B:176–178, 1978, that Boswellia serrata largely contains the following substances:

$\beta$-Boswellic acid, Acetyl-$\beta$-boswellic acid, Acetyl-11-keto-$\beta$-boswellic acid, 11-Keto-$\beta$-boswellic acid.

Pharmacological tests of the prophylactic and/or therapeutic effectiveness of the so-called boswellic acids are not described in the literature in relation to Alzheimer's disease. As a boswellic acid, $\beta$-boswellic acid is preferably used, which according to the literature is isolated from boswellia serrata or other plants known to contain boswellic acid. The $\beta$-boswellic acid can contain low levels of $\alpha$- or $\gamma$-boswellic acid. As physiologically acceptable salts of the boswellic acid, sodium, potassium, ammonium, or calcium salt can be used. As a derivative of the boswellic acid, lower alkyl esters that have been obtained by esterifying the carboxyl group with a $C_1$–$C_6$ alcohol, preferably methylester or ester that has been obtained by esterifying the hydroxyl group with a physiologically compatible carboxylic acid is used. The preferred derivatives are $\mu$-boswellic acid acetate, $\mu$-boswellic acid formate, $\mu$-boswellic acid methylester, acetyl-$\mu$-boswellic acid, acetyl-11-keto-$\mu$-boswellic acid and 11-keto-$\mu$-boswellic acid. According to the invention it is further possible to use a medication from a plant containing boswellic acid. It is preferable according to the invention to use medicaments won from incense or incense resins.

Plants that contain boswellic acid are incense plants of the boswellia type, especially: Boswellia (serrata, papyrifera, frereana, carteri, thurifera, glabra, bhaw-dajiana, oblongata, socotrana and other representatives of this family).

A particularly preferred botanical medicament containing boswellic acid is Phytopharmakon H 15, a lipophilic extract from the boswellia serrata, distributed by the company Ayurmedica in Pöcking. This prescription drug contains a dry extract made from olibanum as an ingredient. The commercial product, tablets as well as granulated powder consist of the following: 1 tablet contains 400 mg dry extract from olibanum (4.2–5.9:1), extraction means: chloroform/methanol 1 g granulated powder contains 500 mg dry extract from olibanum (4.2–5.9:1), extraction means: chloroform/methanol.

According to the invention either natural or synthetic compounds can be used.

According to the invention, it is further possible to use the compound together with other chemically pure drugs and/or other botanical drugs.

According to the invention, the medicament is administered as necessary in each case. Since the medicaments which contain the boswellic acids, its salts and derivatives are only slightly toxic, the dosage is not critical and can be varied easily depending on the severity of the illness, the weight of the patient to be treated, the means of administration, the frequency of administration and the duration of the treatment by the doctor.

Single doses, for example, can be administered one to four times daily. The exact dosage depends on the means of administration and the condition to be treated. Of course, it can be necessary to make routine variations in the dosage, according to the age and weight of the patient in each case as well as the severity of the diseased condition to be treated.

The medications used in accordance with the invention can be formulated in known ways with the use of one or more pharmaceutically acceptable agents or diluents. The medicament can be formulated for oral, parenteral, rectal or intranasal administration or in a way suited to administration by inhalation or insufflation. Preparations of the compounds for oral administration are preferred.

The pharmaceutical preparations for oral administration can exist in the form of tablets or capsules, which are produced by known methods with pharmaceutically acceptable diluent and binding agents (i.e., pregelatinized cornstarch, polyvinylpyrrolidone or hydroxypropyl methylcellulose), filler (i.e., lactose, sucrose, mannitol, cornstarch, microcrystalline cellulose or calcium hydrogen phosphate); liniment (i.e., stearic acid, polyethylene glycol, magnesium stearate, talc or silicon dioxide); disintegration agent, (i.e., potato starch, sodium starch glycolate or sodium carboxymethylcellulose); or wetting agent (i.e., sodium lauryl sulfate). The tablets can be covered by a known method.

Liquid preparations for oral administration can exist, for example, as aqueous or oily solutions, syrups, elixirs, emulsions or suspensions, or they can exist as a dry product to be constituted with water. Such liquid medicaments can be produced by known methods with pharmaceutically acceptable ingredients such as suspension agents (i.e., sorbitol syrup, cellulose derivitives, glucose/sugar syrup, gelatine, aluminum stearate gel or hydrogenized edible fats); emulsifying agent (i.e., lecithin, acacia gum or sorbitan monooleate); non-aqueous agents (i.e., almond oil, oily esters, ethylalcohol or fractionated vegetable oils); and preservatives (i.e., methyl or propyl-p-hydroxybenzoates or sorbitol acid). The liquid preparations can also contain known buffers, flavoring or aromatic agents, coloring and sweeteners as desired.

For parenteral administration the medicament can be formulated for injection, preferably for intravenous, intramuscular or subcutaneous injection. Medicaments for injection can exist in single dose form, for example in ampoules, or in multiple-dose containers with an added preservative. The preparations can exist as suspensions, solutions or emulsions in oily or aqueous agents and can contain preparatory adjuvants such as suspension, stabilizing and/or dispersion agents and/or agents to stabilize the tonicity of the solution. Alternatively, the active component can exist as a powder to be constituted with a suitable agent, for example sterile pyrogen-free water, before use.

The compounds can also be formulated as a rectal medication such as suppositories, for example, those which contain known suppository bases such as cocoa butter or other glycerides. For intranasal administration the compound can be used as a liquid spray in the form of drops or snuffing powder.

For administration by inhalation the compounds are suitably supplied in the form of an aerosol spray from a pressurized package by use of a suitable propellant or in an atomizer. In the case of an aerosol under pressure, the unit of dosage is determined by a valve which is provided to release a measured amount. Capsules and cartridges made of, for example, gelatine for use in a device for inhalation or insufflation can be prepared in such a way that they contain a powder mix made from a compound in accordance with this invention and a suitable powder base, such as lactose or starch.

The following examples explain the application in accordance with the invention.

EXAMPLE 1

| H15 Ayurmedica | |
|---|---|
| H15 tablets at 400 mg | |
| Boswellia serrata extract | 41.0 kg |
| Sterilized lactose | 14.0 kg |
| Sterilized aerosol | 2.0 kg |
| Sterilized M.C.C.P. | 4.0 kg |
| Sterilized starch | 3.0 kg |
| Sterilized magnesium stearate | 1.0 kg |
| Sterilized talc | 2.0 kg |
| Sterilized sodium starch glycolate | 1.0 kg |
| Total: | 68.0 kg |

The boswellia serrata extract is mixed with the remaining ingredients and pressed into tablets in the known fashion.

EXAMPLE 2

| Tablets for oral administration | |
|---|---|
| A. Direct compression | |
| 1) | |
| a) Various extracts from incense (olibanum) | |
| b) Pulverized drug | 0.5–1.0 g/tablet and |
| c) Active ingredient: boswellic acid | 15–30 mg/tablet |
| Magnesium stearate BP | 0.65 mg/tablet |
| Water-free lactose | 80 mg/tablet |

The active ingredient is mixed with the water-free lactose and the magnesium stearate and the mixture is strained. The resulting mixture is pressed into tablets with use of a tableting machine.

| 2) | |
|---|---|
| a) Various extracts from incense (olibanum) | |
| b) Pulverized drug | 0.5–1.0 g/tablet and |
| c) Active ingredient: boswellic acid | 15–30 mg/tablet |
| Magnesium stearate BP | 0.7 mg/tablet |
| Microcrystalline cellulose NF | 100 mg/tablet |

The active ingredient is strained and mixed with the microcrystalline cellulose and the magnesium stearate. The resulting mixture is pressed into tablets with use of a tableting machine.

| B) Wet granulation | |
|---|---|
| a) various extracts from incense (olibanum) | |
| b) pulverized drug | 0.5–1.0 g/tablet and |
| c) active ingredient: boswellic acid | 15–30 mg/tablet |
| Lactose BP | 150.0 mg/tablet |
| Starch BP | 30.0 mg/tablet |
| Pregelatinized cornstarch BP | 15.0 mg/tablet |
| Magnesium stearate BP | 1.5 mg/tablet |

The active ingredient is strained through a suitable strainer and mixed with the lactose, the starch and the pregelatinized cornstarch. Suitable volumes of purified water are added and the powder is granulated. After drying, the granulated powder is strained and mixed with the magnesium stearate. The granulated powder is pressed into tablets with use of a hollow punch. Tablets of other compositions can be produced by changing the ratio between the active ingredient and the lactose or the compression weight and using the appropriate hollow punch.

EXAMPLE 3

Capsules

| | | |
|---|---|---|
| a) | Various extracts from incense (olibanum) | |
| b) | Granulated drug | 0.5–1.0 g/tablet |
| c) | Active ingredient: boswellic acid | 15–30 mg/tablet |
| Free flowing starch | | 150.00 mg/capsule |
| Magnesium stearate BP | | 1.00 mg/capsule |

The active ingredient is sifted and mixed with the other components. Hard gelatine capsules No. 2 are filled with the mixture with the use of a suitable device. Other capsules can also be made by changing the filling weight and by correspondingly changing the capsule size.

EXAMPLE 4

Syrup

| Sucrose-free preparation | | mg/5 ml dose |
|---|---|---|
| a) | Various extracts from incense (olibanum) | |
| b) | Granulated drug and | |
| c) | Active ingredient: boswellic acid | 15–30 |
| Hydroxypropyl methylcellulose USP (Viscosity type 4000) | | 22.5 |
| Buffer<br>Flavoring<br>Coloring<br>Preservatives<br>Sweeteners | | } as desired |
| Purified water | | to 5.0 ml |

The Hydroxypropyl methylcellulose is dispersed in hot water, cooled and then mixed with an aqueous suspension agent, which contains the active ingredient and the other components. The resulting solution is adjusted by volume and mixed.

EXAMPLE 5

| Suspension | | mg/5 ml dose |
|---|---|---|
| a) | Dried drug extract from incense (olibanum) | |
| b) | Pulverized drug | 0.5–1.0 and |
| c) | Active ingredient: boswellic acid | 15–30 |
| Aluminum monostearate | | 75.00 |
| Sweeteners<br>Flavoring<br>Coloring | | } as desired |
| Fractionated coconut oil | | to 5.00 |

The aluminum monostearate is dispersed in approximately 90% of the fractionated coconut oil. The resulting suspension is heated to 115° C. while stirring and then cooled. The sweeteners, flavoring and coloring are added and the active ingredient dispersed. The suspension is adjusted by volume with the rest of the fractionated coconut oil and mixed.

EXAMPLE 6

Sublingual tablets

| | | |
|---|---|---|
| a) | Drug extract from incense (olibanum) | 0.5–1.0 g/tablet |
| b) | Active ingredient: boswellic acid | 15–30 mg/tablet and |
| c) | Pulverized drug | |

-continued

Sublingual tablets

| Compressible sugar NF | 50.5 mg/tablet |
|---|---|
| Magnesium stearate BP | 0.5 mg/tablet |

The active ingredient is sifted through a suitable sifter, mixed with the other components and compressed using a suitable perforated punch. Tablets of other strengths can be produced by changing the ratio of active ingredient to agent or the compression weight.

EXAMPLE 7

Suppository for rectal administration

| | | |
|---|---|---|
| a) | Extracts from incense (olibanum) | |
| b) | Active ingredient: boswellic acid | 15–30 mg and |
| c) | Witepsol H15+ | to 1.0 g |

+suitable quality from hard fat Ph. Eur.

A suspension of the active ingredient in melted witepsol is produced and 1-g suppository forms are filled with the use of a suitable device.

EXAMPLE 8

Injection for intravenous administration

| | | |
|---|---|---|
| a) | Extracts from incense (olibanum) and | |
| b) | Active ingredient: boswellic acid | 15–30 mg/ml |
| Sodium chloride intravenous infusion, BP, 0.9% weight/volume | | to 1 ml |
| Differential value: | | 2500 ml |

The active ingredient is dissolved in a portion of the sodium chloride intravenous infusion, the solution adjusted to volume with the sodium chloride intravenous infusion and the solution is thoroughly mixed. Type 1, 10-ml glass ampoules are filled with the solution and are sealed by melting the glass with nitrogen in the end space. The ampoules are sterilized by heating them in the sterilizer at 120° C. for not less than 20 minutes.

EXAMPLE 9

Cartridges for inhalation

| | | |
|---|---|---|
| a) | Extracts of incense (olibanum) and | |
| b) | Active ingredient (micronized): boswellic acid | 15–30 mg/cartridge |
| Lactose BP | | 25.00 |

The active ingredient is micronized in a micronizer to a fine particle size and then mixed with the lactose. Hard gelatine capsules No. 3 are then filled with the powder mixture.

EXAMPLE 10

Nasal spray

| | | |
|---|---|---|
| a) | Extracts from incense (olibanum) and | |
| b) | Active ingredient: boswellic acid | 1.5–3.0% by volume |
| Preservatives<br>Sodium chloride BP | | } as desired |

-continued

| Nasal spray | |
|---|---|
| Purified water BP | to 100 |
| Yield weight: | 100 mg (equivalent to 7 mg active ingredient) |

The active ingredient, the preservatives and the sodium chloride are dissolved in a portion of the water. The solution is adjusted to volume with water and the solution is thoroughly mixed.

Case examples

The so-called Phytopharmakon H 15 is administered in therapy mostly as a tablet. While the top dosage is 3×2 tablets daily, the patient generally takes 3×1 tablet daily after eating over a longer period of time.

After three to six weeks a distinct improvement in the overall clinical picture of the treated patient is achieved.

For prophylactic use 2×1 tablets to 3×1 tablets are administered daily after eating over several months for continual prevention.

The effectiveness of the therapy is illustrated by the following case examples.

Case example 1

An 83 year old female patient who has shown the symptoms of Alzheimer's disease for two years (memory reduction, verbal difficulties, inferior cognitive function, aggression), took 3×1 tablet of the Phytopharmakon H 15 per day for a month. Four weeks after beginning therapy, an initial clearing and distinct reduction of the patient's "confusion" could be observed. Continuing therapy over the next several months (2×1 tablet H 15 per day) leads to a distinct and constant improvement of the general clinical findings which are confirmed by the patient's family members.

Case example 2

An 81 year old male Alzheimer's patient was treated over a period of three weeks with a dosage of 3×2 tablets of H 15 daily. The dosage was subsequently cut in half (3×1 tablet of H 15 daily). The verbal difficulties, disorientation and deficit of cognitive capabilities were clearly better after the fourth week. With the reduction of therapy to 3×1 tablets, progress seemed to come to a standstill for about four weeks, but then further improvement occurred in all deficits.

Case example 3

A 79 year old male Alzheimer's patient with changing symptoms (primarily disrupted orientation, misjudgment of reality, strong mood swings with aggression) took 3×1 tablets daily.

The disrupted orientation clearly is subsiding after three weeks and the patient recognizes his surrounding relatives again with increasing regularity. His mood is becoming more stable, the aggressive outbreaks are subsiding and his speech is becoming more orderly.

Case example 4

A 63 year old female patient, who suffers from the advanced stages of Alzheimer's disease (the diagnosis was made four years ago; the patient no longer recognizes her children and is completely disoriented and decompensated with regard to higher human control functions such as bowel movement and feeding), was given 3×1 tablet H 15 daily. After three weeks the first recognizable improvement in her overall state could be noticed, which although slow, progressed steadily.

Case example 5

A 59 year old female Alzheimer's patient who has suffered from this disease for five years and shows the corresponding symptoms, is disoriented, no longer recognizes her surroundings or relatives and for this reason has required nursing care. A treatment of 3×2 tablets H 15 daily is leading to an improvement in her clinical picture after four weeks.

I claim:

1. A method for treating Alzheimer's disease which comprises administering to a patient in need of such treatment, an effective dosage of a medicament comprising at least one of the following: incense (olibanum), incense extract, biologically active substances contained in incense, derivatives and physiologically acceptable salts thereof, boswellic acid, derivatives and physiologically acceptable salts thereof.

2. The method of claim 1, wherein the medicament comprises at least one of the following:

β-boswellic acid, acetyl-β boswellic acid, acetyl-11-keto-β-boswellic acid, 11-keto-β-boswellic acid, or physiologically acceptable salts and derivatives thereof.

3. The method of claim 2, wherein said physiologically acceptable salts comprises a sodium, potassium, ammonium or calcium salt of β-boswellic acid.

4. The method of claim 1, wherein said derivatives of boswellic acid comprise lower alkyl esters of β-boswellic acid.

5. The method of claim 4, wherein said lower alkyl esters of β-boswellic acid are selected from the group consisting of β-boswellic acid, acetate, β-boswellic acid formate, β-boswellic acid methylester, acetyl-β-boswellic acid, acetyl-11-keto-β-boswellic acid and 11-keto-β-boswellic acid.

6. The method of claim 1, wherein said incense or incense extract is obtained from boswellia serrata.

7. The method of claim 1, wherein said medicament is administered intraperitoneally, orally, buccally, rectally, intramuscularly, topically, subcutaneously, intra-articularly or intravenously.

8. The method of claim 1, wherein said medicament is in the form of tablets, coated tablets, capsules, injectable solutions, solutions, emulsions, salves, cremes, inhalatories, aerosol sprays or suppositories.

* * * * *